United States Patent [19]

Groll et al.

[11] Patent Number: 4,689,197
[45] Date of Patent: Aug. 25, 1987

[54] PROCESS FOR THE PRODUCTION OF A METALLIC DENTURE

[75] Inventors: Werner Groll, Karlstein; Josef Rothaut, Fort Lee; Angela Klaus; Rudi Steinke, both of Hanau, all of Fed. Rep. of Germany

[73] Assignee: Degussa Aktiengesellschaft, Frankfurt am Main, Fed. Rep. of Germany

[21] Appl. No.: 848,211

[22] Filed: Apr. 4, 1986

[30] Foreign Application Priority Data

Sep. 11, 1985 [DE] Fed. Rep. of Germany ....... 3532331

[51] Int. Cl.$^4$ ............................................. B22F 1/00
[52] U.S. Cl. ................................... 419/23; 29/160.6; 75/232; 75/235; 106/35; 264/16; 264/17; 427/2; 419/19; 419/32; 419/36; 428/552
[58] Field of Search ................. 433/199, 200; 264/16, 264/17; 106/35; 29/160.6; 419/19, 23, 32, 36; 428/552; 427/2; 75/232, 235

[56] References Cited

U.S. PATENT DOCUMENTS

| Re. 29,093 | 12/1976 | Burns | 419/66 |
|---|---|---|---|
| 3,933,961 | 1/1976 | Burns | 419/63 |
| 4,277,283 | 7/1981 | Tobioka et al. | 419/18 |
| 4,431,449 | 2/1984 | Dillon et al. | 428/567 |
| 4,434,211 | 2/1984 | Shoher et al. | |

FOREIGN PATENT DOCUMENTS

| 104320 | 4/1984 | European Pat. Off. |
| 1915977 | 10/1970 | Fed. Rep. of Germany |

Primary Examiner—Stephen J. Lechert, Jr.
Attorney, Agent, or Firm—Cushman, Darby & Cushman

[57] ABSTRACT

A denture with a metallic microstructure and with low shrinkage and porosity is produced by metallurgical sintering by providing a multimodal size distribution of coarse and fine fractions of metal powder, optionally also with glass or ceramic powder, converting this powder mixture with water into a slip, modelling the denture with this, and sintering the slip at a temperature which exceeds the solidus temperature of at least one component of the powder mixture.

22 Claims, No Drawings

PROCESS FOR THE PRODUCTION OF A METALLIC DENTURE

BACKGROUND OF THE INVENTION

The invention relates to a method of producing a denture which can be veneered with ceramic or plastics with a metallic microstructure by sintering technology, from a mixture of metal powders and if necessary glass or ceramic powders. A mixing liquid is added to the powder mixture to form a spreadable mass with which the denture is modelled using techniques conventional in dental ceramics on a ceramic model of the prepared tooth used as a bat and is subsequently sintered on the model.

Production of a metallic denture for prosthetic treatment in the case of dental sickness or after loss of one or several teeth, as for example inlays, crowns and bridges which can be veneered with ceramic or plastic, or crowns and bridges which are not veneered is done usually with the so-called "lost wax technique", a precise casting technique which ensures good dimensional accuracy.

The advantages of crowns and bridges produced in this manner include not only dimensional accuracy but primarily high strength and ductility which must be ensured in the case of larger bridge structures to prevent forced ruptures in the case of overload. On the other hand, the process itself is very time consuming, material— and equipment—intensive. Because runner bars and spryes are necessary in the case of the lost wax method, a much higher amount of alloy must be used vis-a-vis the weight of the cast denture; this can lead to changes of alloy properties in case of multiple reuse and if not reused it remains as scrap. Another disadvantage of this technique is that in the case of defects in the cast item, repair is not possible, but the entire production process beginning with wax modeling must be repeated.

Another method for producing jacket crowns reinforced with metal caps is described in European application No. 0104320. A preformed, folded cap of a metal foil preferably built up from several layers of different metals is placed over the model of the prepared tooth and rotated onto the latter with a suitable tool. When annealed with a Bunsen burner, the superposed folds are sealed, resulting in a metal cap with a wall thickness of roughly 100 microns which is then veneered with a dental ceramic. Cost of labor and equipment is considerably reduced compared to the lost wax method; however, the denture produced in this manner falls far short of the strength properties of a cast denture so that bridges cannot be produced with this process. In addition, the uniform thickness of the metal foil in the case of highly prepared teeth or in the case of large teeth, especially molars, requires a very thick ceramic veneer so that the danger of ceramic failure is very great, especially in the case of posterior teeth.

A known method for producing full ceramic crowns is the jacket crown technique in which an aluminum oxide containing ceramic mass is applied to a platinum foil preformed to the shape of the prepared tooth and is sintered. The crown is modeled freely by hand so that the entire equipment necessary to produce cast crowns is not required. The properties of the ceramic mass allow exact modelling of the most complex tooth shapes. The major disadvantage of this type of denture is the brittleness, a characteristic property of ceramic material, which leads to catastrophic failure in the case of sudden overload. Furthermore the strength is not adequate to produce thick walled crowns and larger bridges.

German OS No. 19 15 977 describes a method for producing a denture based on metal or alloy powders with a particle size from 2 to 25 microns which are made into a paste using a binder volatile below the sintering temperature. This paste is freely modelled using a spatula on a exact model of the prepared tooth; the model is used as a bat. The binder is expelled at higher temperatures and the metal particles sintered together. However, this method is subjected to the disadvantage that a high densification of the metal powder mixture cannot be achieved with the paste so that relatively great shrinkage takes place during sintering. The exact fit required for a denture cannot be achieved with this process, even when very fine, spherical powders are used, which on the other hand can only be produced with relatively low output and, therefore, only at high costs.

SUMMARY OF THE INVENTION

The task of the invention was to develop a method for producing a denture which can be veneered with ceramic or plastic with a metallic microstructure using sintering technology from a mixture of metal powders and if necessary glass or ceramic powders. A mixing liquid is added to the powder mixture to form a spreadable mass with which the denture is modelled with techniques ordinarily used in dental ceramics on a ceramic model of the prepared tooth being used as a bat and is then sintered on the model. In this process shrinkage should be minimized during sintering to maintain a denture with exact fit and with high strength which is for the most part free of open porosity and which can be produced inexpensively.

This was done by the invention as follows. The powder mixture has a multimodal size of coarse and fine fractions in which the grain size of the coarsest fraction should not exceed 100 microns. Adding water this powder mixture is converted into a slip. The sintering temperature of the slip composition is selected such that it exceeds the solidus temperature of at least one component of the powder mixture and if the sintered body should be veneered with dental ceramic exceeds the baking-on temperature of the ceramic by at least 50° C.

Preferred versions of the method are set forth in the dependent claims.

In the method of the invention, a mixture of metal powders of the elements necessary for desired alloy composition in the corresponding quantitative ratios or alloyed powders and in a given case ceramic powders is mixed with water to form a slip with consistency and modelling properties corresponding to conventional dental or veneering ceramics. To maximize bulk density and accordingly minimize shrinkage during sintering, the use of powder mixtures with multimodal size distributions of the metal or ceramic powders used has been found to be essential in which the powders with grain size less than 100 microns must be used. The percentage of ceramic powder should only be of such a magnitude that a metallic matrix is always ensured. The admixed slip is modelled on an exact model of the prepared tooth using techniques and equipment conventional in dental ceramics and is compacted by suitable techniques likewise known in production of ceramic teeth or ceramic veneers (for example, vibrating with the fluted part of a modelling instrument). During the compaction process liquid is expelled; in this way the powder particles can be rearranged into more favorable positions and moved closer together. The model used, consisting of a refractory ceramic, is preferably enlarged for modelling with suitable materials according to known shrinkage of the alloy and insulated against overly great liquid absorption.

These procedures yield optimum bulk density of the densified slip and low shrinkage during sintering. To achieve high sintering density a sintering method must be used in which the sintering temperature exceeds the solidus temperature of at least one component of the mixture, whereby efforts must be made to ensure that the sintering temperature exceeds the baking-on temperature of the ceramic by at least 50° C. in the case of intended ceramic veneering. The latter condition must be satisfied to prevent deformation of the metal framework. Depending on the alloy composition. sintering is done in air (for example, precious metals), in a protective gas atmosphere or under a vacuum. After sintering a sufficiently dense denture with a metallic matrix results.

Multimodal means that powder mixtures are used with a size distribution with several peaks for different particle sizes.

To achieve a high bulk density of the slip mass, those powder mixtures are especially suitable which contain coarse fractions in the range between 30 microns and 100 microns with a percent by volume from 30 to 90% in the overall powder mixture and which exhibit preferably spherical form. As fine powder (less than 50 microns) any form can be used; however, likewise spherical or fleshy powders are preferred.

Preferably, the powder components with a solidus temperature greater than the sintering temperature of the slip composition are added as the coarse fraction, while the powder components with a solidus temperature less than the sintering temperature of the slip composition are added as the fine component. If the higher melting components are added as the fine fraction, a rigid skeleton can be formed, because the powder particles sinter during drying or when heated to the firing temperature. Thus densification by particle rearrangement can not occur during liquid phase sintering. The liquid phase which is formed when the liquidus temperature of the low melting powder components is exceeded penetrates into the porous skeleton of the high melting component so that sites previously occupied by them remain as pores.

Favorable sintering temperatures for producing a denture using sintering technology are those in the range between the solidus temperature of the sintered alloy $T_{solidus}$ and ($T_{solidus} - 200°$ C.;) here the boundary conditions that at least one powder component must have a solidus temperature less than sintering temperature and that the sintering temperature in the case of ceramic facing must lie 50° C. above the baking-on temperature of the ceramic must be considered. The liquid phase can be consumed in full or in part during the sintering process caused by alloy formation which takes place. The use of the described sintering temperatures in the range between $T_{solidus}$ and ($T_{solidus} - 200°$ C.) presupposes that the powder mixture consists of at least two metal or alloy powders with different solidus temperatures.

In the case that powder mixtures consist of different fractions of only one alloy, a sintering temperature between $T_{solidus}$ and $T_{liquidus}$ can be used to advantage. Part of the alloy is then present as a liquid phase, according to the solid/liquid phase relation. The liquid phase should occur here only to such an extent that stability of the shape of the sintered compact is preserved during sintering.

To produce bridges, prefabricated parts, as, for example, wires, sections or metal pouches can be used which are incorporated into the slip during modelling of the crown caps and fixed there by sintering or soldered to the sintered caps. This procedure allows a better fit since the prefabricated parts do not shrink during sintering. another possibility for producing bridges consists in producing the individual teeth as well as the pouches using the method of the invention and then soldering them.

To improve fit of the denture, the model of the prepared tooth can be coated with a material which burns without residue, for example wax. The thickness of the coating is such that the circumferential enlargement corresponds to expected shrinkage of the slip composition during sintering. The slip is applied to this coating and condensed. The material which burns without residue is then burned off at a suitable temperature. During sintering the shaped item (for example, a crown) shrinks onto the model so that its shape is accurately reproduced.

In addition, before applying the slip, the bat can be coated with a metal which exhibits a melting point higher than that of the alloy to be sintered. Then the slip is applied to the model of the prepared tooth prepared in this manner and liquid phase sintered. The liquid phase wets the metal-coated model and ensures that the alloy fits the form closely even at the margin of the ceramic model.

To produce the slip metal powder mixtures are mixed with water preferably containing electrolytes, as, for example, sodium carbonate, sodium hydroxide, or strontium chloride. Mono- or multivalent alcohols can also be added to the water. Thus, there can be added methyl alcohol, ethyl alcohol, isopropyl alcohol, ethylene glycol or glycerine.

To produce a well-fitting denture using sintering technology, the green density of the slip composition should be as high as possible before sintering to minimize shrinkage during sintering. This is done as follows. Powder mixtures consisting of one or several metals or metal alloys with bi- or multimodal size distribution are used in which both spherical or fleshy particles or those in any other form can be used. Table 1 lists selected examples of powder combinations. Gold, platinum, and palladium powder of different size distributions and particle forms were used as model powders. Pure spherical powders (material 1) yield a higher base density than pure flaky powders (material 6). The two materials, however, lie outside the invention. By adding additional powders of smaller particle size to multimodal powder mixtures the green density can be significantly increased. The best results are achieved with slip masses with a coarse fraction consisting of spherical particles (Materials 1-5).

In addition to size distribution, size and form of the powder used, the sintering temperature is of decisive importance for attainable density and strength. Table 2 lists the properties of sintered alloy Au50 Pt35 Pd15 when using different powder mixtures with multimodal size distribution after sintering. The density values and yield strength 0.2% offset are favorable for use as crown and bridge materials. The yield strengths 0.2% offset of conventional cast dental and bridge alloys likewise fall in the range from 450 to 600 MPa. Alloys produced in this manner exhibit closed porosity; this is important for prevention of plaque deposits and sites of preferred corrosion. Bending tests were carried out for alloys 5 and 7 using specimens 35 mm long with a cross-section 3×3 mm2. The yield strengths observed in the bending test match those of the pressure tests. The sintered alloys, therefore, exhibit sufficient strength vis-a-vis tensile stresses. The considerably higher bending rupture strength $R_m$ confirms that plastic deformation takes place before rupture.

Base metal containing alloys were also used to produce specimens. To do this, for example, atomized powder of an Au-Sn-In alloy was mixed with Au and Pt powder and sintered at 990° C. To prevent oxidation of Sn and In, the samples to be sintered were placed in a graphite box on a ceramic base and sintered in this box in a conventional ceramic furnace.

The compositions can comprise, consist essentially of, or consist of the stated materials.

DETAILED DESCRIPTION

The following examples will explain the invention in greater detail:

EXAMPLE 1

A duplicate consisiting of a refractory, castable ceramic is produced from a master model; the duplicate is later used as the bat. A wax cap is modelled on the duplicated model made of refractory ceramic; the wall thickness of the cap is roughly 0.3 mm. On the one hand, the wax performs the function of insulation against the model stump and on the other hand is used to enlarge the model to compensate for shrinkage which occurs during sintering. The wax cap can be formed from a wax sheet (thickness 0.3 mm) or produced using a dipping wax.

A slip is applied to the model prepared in this manner; the slip contains 10% by volume $TiO_2$ and 90% by volume of a metal-powder mixture. The latter consists of 74.4% by weight Au powder (spherical) with a particle size less than 90 microns, 18.6% by weight Au powder (flaky) with a particle size less than 10 microns and 7% by weight Pt powder (flaky) with a particle size less than 15 microns. Water with 0.5 g/l strontium chloride is used as the mixing liquid. The slip exhibits properties corresponding to those of dental ceramic slips. A veneerable crown cap is made with the slip using techniques conventional in modelling with dental ceramics and tools used for this purpose (brush, spatula, fluting tool, etc.). Upon completion of modelling, the entire configuration is kept for 30 minutes in a dewaxing furnace at 200° C. During this time the wax burns off without residue. Afterwards, the dewaxed configuration is first placed in the drying chamber of the ceramic furnace and dried at 600° C. for 15 minutes, then moved into the firing chamber preheated to 1200° C. and sintered 15 minutes there.

After sintering the crown cap is cooled in air and can then be removed from the bat. Ceramic is applied directly to the sintered cap in conventional fashion without intermediate treatment. The crown produced in this manner features a metallic matrix and good fit, in concert with a high strength.

EXAMPLE 2

The model is produced and prepared as described in Example 1. The slip admixed with water consists of 10% by volume of $TiO_2$ and 90% by volume of metal powder mixture which in turn consists of 65.1% by weight Au powder (spherical) of fraction 36-25 microns, 27.9% by weight Au powder (flaky) less than 25 microns and 7% by weight Pt powder (flaky) less than 15 microns. A crown with a occlusal surface is modelled with this slip using techniques conventional in ceramic veneering. Due to the outstanding modelling capacity of the slip, fine details on the occlusal surfaces can be formed. The stages of wax removal, drying and sintering proceed as in Example 1. After sintering, the crown is removed from the bat, the surface fine ground and subsequently polished. This crown also has a good fit. No pores can be recognized.

The entire disclosure of German priority application No. P3532331.0 is hereby incorporated by reference.

As used in the claims, the term metal is intended to cover pure metals and alloys of two or more metals.

TABLE 1

| Material | Powder form/-size P1 | P2 | (μm) □ platelets \| needles P3 | spherical P4 | Composition in % by weight P1:P2:P3:P4 | rel. Green Density |
|---|---|---|---|---|---|---|
| 1 | 90-71 | — | — | — | 100/—/—/— | 35 |
| 2 | 90-71 | < 10 | — | — | 70/30/—/— | 58 |
| 3 | 90-71 | < 10 | $TiO_2$(<1) | — | 68.42/29.33/2.25/— | 60 |
| 4 | 90-71 | < 10 | $Bi_2O_3$(<2) | — | 66.94/28.68/4.38/— | 73 |
| 5 | 90-71 | □ < 25 | — | — | 90/10/—/— | 56 |
| 6 | □ < 50 | — | — | — | 100/—/—/— | 9.8 |
| 7 | □ < 50 | | < 10 | — | 90/10/—/— | 19 |
| 8 | □ < 50 | □ < 15 (Pt) | □ < 15 (Pd) | — | 50/35/15/— | 25 |
| 9 | □ < 50 | ⊔ < 15 (Pt) | □ < 15 (Pd) | $TiO_2$(<1) | 48.74/34.13/14.63/2.5 | 47 |

TABLE 2

| | Powder form/-size μm 50% Au | 15% Pd | 35% Pt | Ceramic Additive Amount/% by Vol. | Ts/°C. | p/% | Rp 0.2 in MPa compression | Bending test Rp/MPa | Rm/MPa |
|---|---|---|---|---|---|---|---|---|---|
| 1 | □ < 25 | □ < 15 | □ < 15 | | 1200 | 91.8 | 582 +−43 | | |
| 2 | □ < 25 | □ < 15 | □ < 15 | | 1300 | 92.7 | 700 +−8 | | |
| 3 | □ < 25 | □ < 15 | □ < 15 | + 10 Vol % $TiO_2$ | 1200 | 92.0 | 631 +−21 | | |
| 4 | □ < 25 | □ < 15 | □ < 15 | + 20 Vol % $TiO_2$ | 1200 | 91.9 | 656 | | |

TABLE 2-continued

| | Powder form/-size μm | | | Ceramic Additive | Ts/°C. | ρ/% | Rp 0.2 in MPa compression | Bending test | |
|---|---|---|---|---|---|---|---|---|---|
| | 50% Au | 15% Pd | 35% Pt | Amount/% by Vol. | | | | Rp/MPa | Rm/MPa |
| 5 | □ < 25 | □ < 15 | □ < 15 | + 10 Vol % TiO₂ | 1300 | 93.7 | 710 +−16 +−15 | 640 +−30 | 900 +−50 |
| 6 | □ < 25 | □ < 15 | □ < 15 | + 10 Vol % Bi₂O₃ | 1200 | 92.3 | 610 +−20 | | |
| 7 | □ < 50 | □ < 15 | □ < 15 | | 1300 | 91.8 | 630 +−15 | 650 +−50 | 864 +−100 |
| 8 | □ < 50 | □ < 15 | □ < 15 | + 10 Vol % TiO₂ | 1300 | 97.2 | 720 +−20 | | |
| 9 | □ < 25 | < 10 | < 10 | | 1300 | 91.0 | 566 +−5 | | |

□ platelets
spheres

What is claimed is:

1. In a process for the production of a denture, optionally veneered with ceramic or plastic, having a metallic microstructure, using sintering technology, from a mixture of metal powders, optionally together with glass or ceramic powders which mixture is treated with a mixing fluid to form a spreadable mass with which the denture is modelled on a ceramic model of the prepared tooth which is used as bat and then sintered comprising employing a metal powder mixture having a multimodal size distribution of coarse and fine fractions in which the particle size of the coarsest fraction does not exceed 100 microns; converting this powder mixture with water to a slip sintering the slip and selecting the sintering temperature of the slip mass such that it exceeds the solidus temperature of at least one component of the powder mixture and in the case of planned veneering with ceramic exceeds the baking-on temperature of the ceramic by at least 50° C.

2. A process according to claim 1 wherein the denture is veneered with a ceramic or plastic.

3. A process according to claim 1 wherein the powder mixture consists of metal powder.

4. A process according to claim 1 wherein the powder mixture in addition to metal powder contains a minor amount by weight of glass or ceramic powder.

5. A process according to claim 1 wherein th coarse fraction has a particle size between 30 and 100 microns and is of spherical shape and the fine fraction has a particle size below 50 microns and is of any shape, the percent by volume of the coarse fraction being 30 to 90%.

6. A process according to claim 5 comprising adding the powder component having a solidus temperature below the sintering temperature of the slip composition as a fine fraction.

7. A process according to claim 1 comprising adding the powder component having a solidus temperature below the sintering temperature of the slip composition as a fine fraction.

8. A process according to claim 7 wherein the slip composition contains powders of a plurality of metals and the sintering temperature lies in the range between T$_{solidus}$ minus 200° C. and T$_{solidus}$ of the sintered metal but is also above the solidus temperature of a least one of the powder components.

9. A process according to claim 6 wherein the slip composition contains powders of a plurality of metals and the sintering temperature lies in the range between T$_{solidus}$ minus 200° C. and T$_{solidus}$ of the sintered metal but is also above the solidus temperature of at least one of the powder components.

10. A process according to claim 5 wherein the slip composition contains powders of a plurality of metals and the sintering temperature lies in the range between T$_{solidus}$ minus 200° C. and T$_{solidus}$ of the sintered metal but is also above the solidus temperature of at least one of the powder components.

11. A process according to claim 1 wherein the slip composition contains powders of a plurality of metals and the sintering temperature lies in the range between T$_{solidus}$ minus 200° C. and T$_{solidus}$ of the sintered metal but is also above the solidus temperature of at least one of the powder components.

12. A process according to claim 7 wherein the slip composition contains powders of only one alloy and sintering temperature lies between the solidus and liquidus temperature of the sintered metal.

13. A process according to claim 6 wherein the slip composition contains powders of only one alloy and sintering temperature lies between the solidus and liquidus temperature of the sintered metal.

14. A process according to claim 5 wherein the slip composition contains powder of only one alloy and sintering temperature lies between the solidus and liquidus temperature of the sintered metal.

15. A process according to claim 1 wherein the slip composition contains powders of only one alloy and sintering temperature lies between the solidus and liquidus temperature of sintered metal.

16. A process according to claim 13 comprising sintering a low melting metal or a low melting alloy for finishing a surface and closing pores onto the surface of the sintered slip composition.

17. A process according to claim 9 comprising sintering a low melting metal or low melting alloy for finishing a surface and closing pores onto the surface of the sintered slip composition.

18. A process according to claim 1 comprising sintering a low melting metal or a low melting alloy for finishing a surface and closing pores onto the surface of the sintered slip composition.

19. A process according to claim 17 comprising applying a layer consisting essentially of a material which burns without residue to the model used as a bat according to shrinkage during sintering.

20. A process according to claim 13 comprising applying a layer consisting essentially of a material which burns without residue to the model used as a bat according to shrinkage during sintering.

21. A process according to claim 1 comprising applying a layer consisting essentially of a material which burns without residue to the model used as a bat according to shrinkage during sintering.

22. A process according to claim 1 wherein the metal is an alloy.

* * * * *